(12) United States Patent
Kawashima et al.

(10) Patent No.: US 8,700,213 B2
(45) Date of Patent: Apr. 15, 2014

(54) MANEUVERING SYSTEM HAVING INNER FORCE SENSE PRESENTING FUNCTION (75) Inventors: Kenji Kawashima, Yokohama (JP); Kotaro Tadano, Yokohama (JP)

(73) Assignee: Tokyo Institute of Technology, Tokyo (JP)

( * ) Notice: Subject to any disclaimer, the term of this patent is extended or adjusted under 35 U.S.C. 154(b) by 1156 days.

(21) Appl. No.: 12/529,515

(22) PCT Filed: Feb. 29, 2008

(86) PCT No.: PCT/JP2008/053614
§ 371 (c)(1),
(2), (4) Date: Dec. 14, 2009

(87) PCT Pub. No.: WO2008/108289
PCT Pub. Date: Sep. 12, 2008

(65) Prior Publication Data
US 2010/0139436 A1 Jun. 10, 2010

(30) Foreign Application Priority Data
Mar. 1, 2007 (JP) .................. 2007-051390

(51) Int. Cl.
*G06F 19/00* (2011.01)
*B66C 1/42* (2006.01)
*B66B 21/00* (2006.01)
*B25J 17/00* (2006.01)
*B25J 17/02* (2006.01)
*B25J 18/00* (2006.01)

(52) U.S. Cl.
USPC .... 700/245; 294/86.4; 414/744.1; 74/490.01; 901/34

(58) Field of Classification Search
USPC .................. 74/490.01; 414/744.1, 744.8; 318/568.11; 294/86.4, 111; 700/245; 901/30, 34, 36
See application file for complete search history.

(56) References Cited

U.S. PATENT DOCUMENTS 3,575,301 A * 4/1971 Panissidi ................. 414/618
5,784,542 A * 7/1998 Ohm et al. ................ 700/260
(Continued)

FOREIGN PATENT DOCUMENTS

JP 6-55467 3/1994
JP 6-61481 8/1994
(Continued)

OTHER PUBLICATIONS

International Search Report dated Jun. 10, 2008.

*Primary Examiner* — Justin Krause
(74) *Attorney, Agent, or Firm* — Kratz, Quintos & Hanson, LLP (57) ABSTRACT

A compact, lightweight manipulation system that excels in operability and has a force feedback capability is provided. When automatic operation of a slave manipulator 105 that follows manual operation of a master manipulator 101 is bilaterally controlled by means of communication, the force acting on the slave manipulator is fed back to the master manipulator by operating the master manipulator primarily under electrically-driven speed control and the slave manipulator primarily under pneumatically-driven force control. Therefore, in the master manipulator, it is not necessary to compensate for the dynamics and the self-weight of the master manipulator in the motion range of a user, allowing highly accurate, broadband positional control, which is specific to an electrically-driven system, and in the slave manipulator, non-linearity characteristics specific to a pneumatically-driven system presents passive softness, provides a high mass-to-output ratio, and produces a large force.

11 Claims, 10 Drawing Sheets

(56) References Cited

U.S. PATENT DOCUMENTS

| | | | |
|---|---|---|---|
| 5,931,832 A * | 8/1999 | Jensen | 606/1 |
| 6,377,011 B1 * | 4/2002 | Ben-Ur | 318/566 |
| 6,786,896 B1 * | 9/2004 | Madhani et al. | 606/1 |
| 6,994,703 B2 * | 2/2006 | Wang et al. | 606/10 |
| 2004/0149065 A1 * | 8/2004 | Moran | 74/490.04 |

FOREIGN PATENT DOCUMENTS

| | | |
|---|---|---|
| JP | 6-261911 | 9/1994 |
| JP | 7-136173 | 5/1995 |

* cited by examiner

MANEUVERING SYSTEM HAVING INNER FORCE SENSE PRESENTING FUNCTION

TECHNICAL FIELD

The present invention relates to a manipulation system in which automatic operation of a slave manipulator that follows manual operation of a master manipulator is bilaterally controllable by means of communication, and particularly to a manipulation system having a force feedback capability.

BACKGROUND ART

In recent years, surgical operations have been widely practiced in the form of endoscopic surgery to improve QOL (Quality of Life), such as reduction in patient's pain, hospitalization period, and size of the scar associated with the surgery. Endoscopic surgery is performed in such a way that an operator inserts forceps or other related tools through a thin tube (trocar) and performs the surgery while observing images from a laparoscope. Since the scar is smaller than that in open surgery, the burden on the patient is smaller. However, since the operator moves the forceps or other related tools using the abdominal wall as a pivotal point, sufficient degrees of freedom are not provided at the tip of the forceps and hence it is not easy to freely approach the site to be treated. Such a situation requires a highly skilled operator. To reduce the burden on the operator, studies on multi-DOF forceps system have been actively underway, in which robotics technology is used to impart multiple degrees of freedom to the tip of forceps.

The master-slave concept used in commercially available multi-DOF forceps systems has advantages of, for example, capability of remotely and intuitively operating the forceps. To provide more accurate, safer workability, it is desirable to provide force feedback to the operator. To this end, studies on forceps with a force sensor provided in the vicinity of the tip of the forceps are underway. However, such a multi-DOF forceps system using electric actuators to drive the master and slave portions not only cannot feed a minute force back to the operator because of a high reduction ratio, but also has an insufficient movable range and results in a bulky apparatus. Further, attaching a force sensor to the forceps is not an easy task in consideration of practical factors, such as reduction in size, sterilization, and calibration.

To address the above problems, studies on a multi-DOF forceps system are underway, in which pneumatic actuators are used to drive the master and slave portions. A pneumatic actuator, which has nonlinear characteristics, is inferior to an electric actuator in terms of controllability, but has advantages of, for example, presenting passive softness, having a high mass-to-output ratio, and producing a large force without a reduction gear train. For example, a multi-DOF forceps system has been proposed (see the non-patent document 1), in which the slave portion includes a 3-DOF forceps manipulator using pneumatic cylinders and the pressure in each of the pneumatic cylinders is used to estimate the external force acting on the tip of the forceps instead of using a force sensor. Further, a multi-DOF forceps system has been proposed (see the non-patent document 2), which includes a 3-DOF pneumatic manipulator that holds and drives the 3-DOF forceps manipulator described in the non-patent document 1 in a region outside the abdomen.

Non-patent document 1: Bilateral control of multi-DOF forceps system having force sensing capability using pneumatic servo technology, Japan Society of Computer Aided Surgery, pp. 25-31, (2005), Kotaro Tadano, Kenji Kawashima Non-patent document 2: Development of master-slave system having force feedback capability using pneumatically-driven multi-DOF forceps: Development of manipulator for holding forceps, Conference on Robotics and Mechatronics, 1A1-A03, (2006), Kotaro Tadano, Kenji Kawashima

DISCLOSURE OF THE INVENTION

In the multi-DOF forceps system described in the non-patent document 1, the forceps manipulator has only three degrees of freedom, which does not allow the motion of the human hand to be reproduced. In the multi-DOF forceps systems described in the non-patent documents 1 and 2, the forceps manipulator includes a mechanism that converts the linear motion of a pneumatic cylinder into rotational motion, so that reduction in weight of the forceps manipulator is difficult to achieve. Further, the master and the slave portions are configured in the same manner, which does not necessarily provide an optimum structure in terms of operability.

The invention has been made in view of the above problems. An object of the invention is to provide a compact, lightweight manipulation system that excels in operability and has a force feedback capability.

To achieve the above object, the manipulation system having a force feedback capability according to the invention is a manipulation system in which automatic operation of a slave manipulator that follows manual operation of a master manipulator is bilaterally controllable by means of communication. The manipulation system is characterized in that the force acting on the slave manipulator is fed back to the master manipulator by operating the master manipulator primarily under electrically-driven speed control and the slave manipulator primarily under pneumatically-driven force control. Therefore, in the master manipulator, it is not necessary to compensate for the dynamics and the self-weight of the master manipulator in the motion range of a user, allowing highly accurate, broadband positional control, which is specific to an electrically-driven system, and in the slave manipulator, non-linearity characteristics specific to a pneumatically-driven system presents passive softness, provides a high mass-to-output ratio, and produces a large force.

The manipulation system is characterized in that the master manipulator includes a 3-DOF translation unit and a 4-DOF orientation unit connected to the translation unit, and the slave manipulator includes a 3-DOF holding unit and a 4-DOF grip unit held by the holding unit. Such a configuration allows the motion of the human hand on the master manipulator side to be reproduced on the slave manipulator side. Further, the manipulation system is characterized in that the translation unit, the orientation unit, the holding unit, and the grip unit are configured as a delta mechanism, a gimbal mechanism, a combination of a parallel link mechanism and a gimbal mechanism, and a wire mechanism, respectively. The master manipulator and the slave manipulator are thus configured differently from each other, so that the shapes thereof can be optimized in terms of operability. Further, the manipulation system is characterized in that the grip unit includes pneumatic rotary actuators and wires connected to the pneumatic actuators, and the grip unit is driven by pulling motions of the wires in response to the motions of the pneumatic actuators. The grip unit can therefore directly transmit the swing motions of the pneumatic actuators, so that the weight of the slave manipulator can be reduced.

The manipulation system is characterized in that the force acting on the grip unit is estimated from the drive forces of the pneumatic actuators by making use of the back drivability thereof. No force sensor is therefore required on the grip unit, thereby providing advantages of reducing the size of the grip unit, making disinfection of the grip unit easy, and eliminating the need for calibration of the grip unit. The manipulation system is characterized in that compliance-based control is applied to the slave manipulator. Therefore, the slave manipulator will not produce an excessive force. Further, the manipulation system is characterized in that position-based impedance control in which a force control loop includes a motion control loop is applied to the master manipulator, and force-based impedance control in which a motion control loop includes a force control loop is applied to the slave manipulator. Therefore, the slave manipulator can be stably operated by imparting a moderate viscosity effect to the master manipulator. Further, the manipulation system is characterized in that automatic operation of the slave manipulator that follows manual operation of the master manipulator is bilaterally controlled by means of wired communication. The master manipulator can therefore remotely operate the slave manipulator by means of the Internet.

DESCRIPTION OF REFERENCE NUMERALS AND SYMBOLS 31 computer
32 servo amplifier
71 computer
72 servo valve
73 air supplier
74 pressure gauge
100 multi-DOF forceps system
101 master manipulator
103 master controller
105 slave manipulator
107 slave controller
110 translation unit
112 motor
113 link
114 parallel link
120 orientation unit
122 first motor
124 second motor
126 third motor
129 force sensor
132 manipulator finger
150 holding unit
153 parallel link
155, 156, 157 pneumatic cylinder
160 grip unit
170 forceps
171 forceps shaft
172 forceps finger holder
173, 174 forceps finger
180 forceps holding unit
182, 183, 184, 185 pneumatic rotary actuator
186, 187, 188, 189 rotary encoder and pressure sensor
191, 192 pressure gauge
193 servo valve
194 regulator
195 air supplier

BEST MODE FOR CARRYING OUT THE INVENTION

An embodiment of the invention will be described with reference to the drawings. The embodiment, which will be described below, does not limit the inventive aspects according to the claims, and of all the combinations of the features described in the embodiment are not necessarily essential in providing means for solving the problems.

Figure 1:
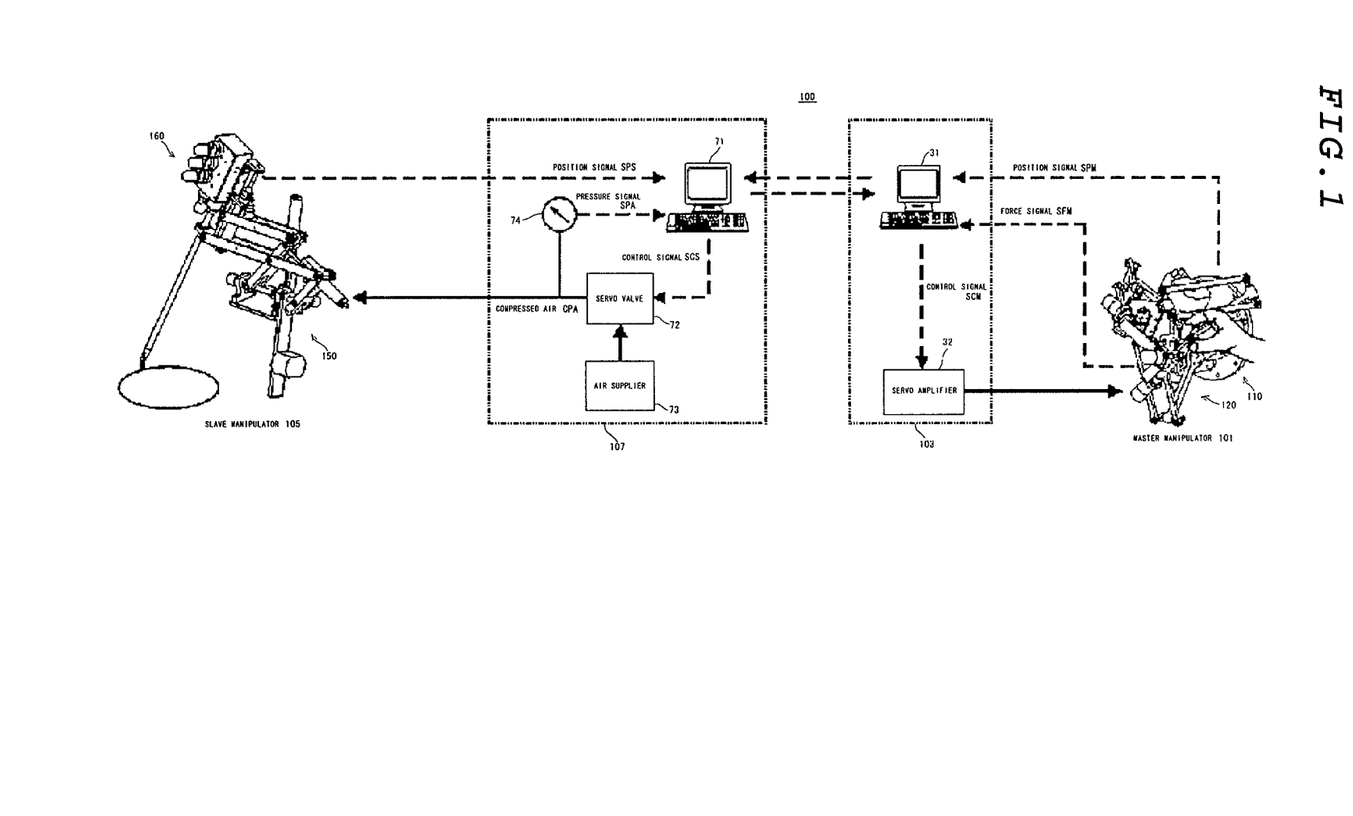
FIG. 1 is a schematic configuration diagram showing a manipulation system having a force feedback capability according to an embodiment of the invention.

FIG. 1 is a schematic configuration diagram showing a manipulation system having a force feedback capability according to an embodiment of the invention. The manipulation system having a force feedback capability is a multi-DOF forceps system 100 including a master manipulator 101, a master controller 103, a slave manipulator 105, and a slave controller 107. The multi-DOF forceps system 100 is a remote manipulation system in which automatic operation of the slave manipulator 105 that follows manual operation of the master manipulator 101 is remotely controllable by means of wired communication between the master controller 103 and the slave controller 107.

The master manipulator 101 primarily operates under electrically-driven positional control using electric actuators, and includes a 3-DOF translation unit 110 configured as a delta mechanism and a 4-DOF orientation unit 120 connected to the translation unit 110 and configured as a gimbal mechanism. On the other hand, the slave manipulator 105 primarily operates under pneumatically-driven force control using pneumatic actuators, and includes a 3-DOF holding unit 150 configured as a combination of a parallel link mechanism and a gimbal mechanism and a 4-DOF grip unit 160 held by the holding unit 150.

Use of an electric actuator, particularly a combination of a high reduction-ratio gear train and an electric motor, has advantages over the case where a pneumatic cylinder is used, for example, in that highly accurate, broadband positional control is possible, and that applying motion control-based force control eliminates the need for compensation for the dynamics and the self-weight of the master manipulator 101 in the motion range of the operator. On the other hand, a pneumatic actuator, which has nonlinear characteristics, is inferior to an electric actuator in terms of controllability, but has advantages, for example, presenting passive softness, having a high mass-to-output ratio, and producing a large force without a reduction gear train.

The master controller 103 includes a computer 31 and a servo amplifier 32. The slave controller 107 includes a computer 71, a servo valve 72, an air supplier 73, and a pressure gauge 74. The computer 31 in the master controller 103 sends a tip position signal, which is obtained by performing kinetic computation on a signal SPM from each encoder in the master manipulator 101, to the computer 71 in the slave controller 107 using UDP/IP communication. The computer 71 in the slave controller 107 sends a control signal SCS to the servo valve 72 based on the received position signal. The servo valve 72 adjusts compressed air CPA from the air supplier 73 based on the received control signal SCS, and supplies the adjusted compressed air to the slave manipulator 105, so that the operation of the slave manipulator 105 is automatically controlled to follow the manual operation of the master manipulator 101.

On the other hand, the computer 71 in the slave controller 107 sends a calculated target value of the force produced at the tip to the computer 31 in the master controller 103 using UDP/IP communication. The computer 31 in the master controller 103 sends a control signal SCM to the servo amplifier 32 based on the received force signal. Based on the received control signal SCM, the servo amplifier 32 feeds the force acting on the slave manipulator 105 back to the master manipulator 101.

Figure 2:
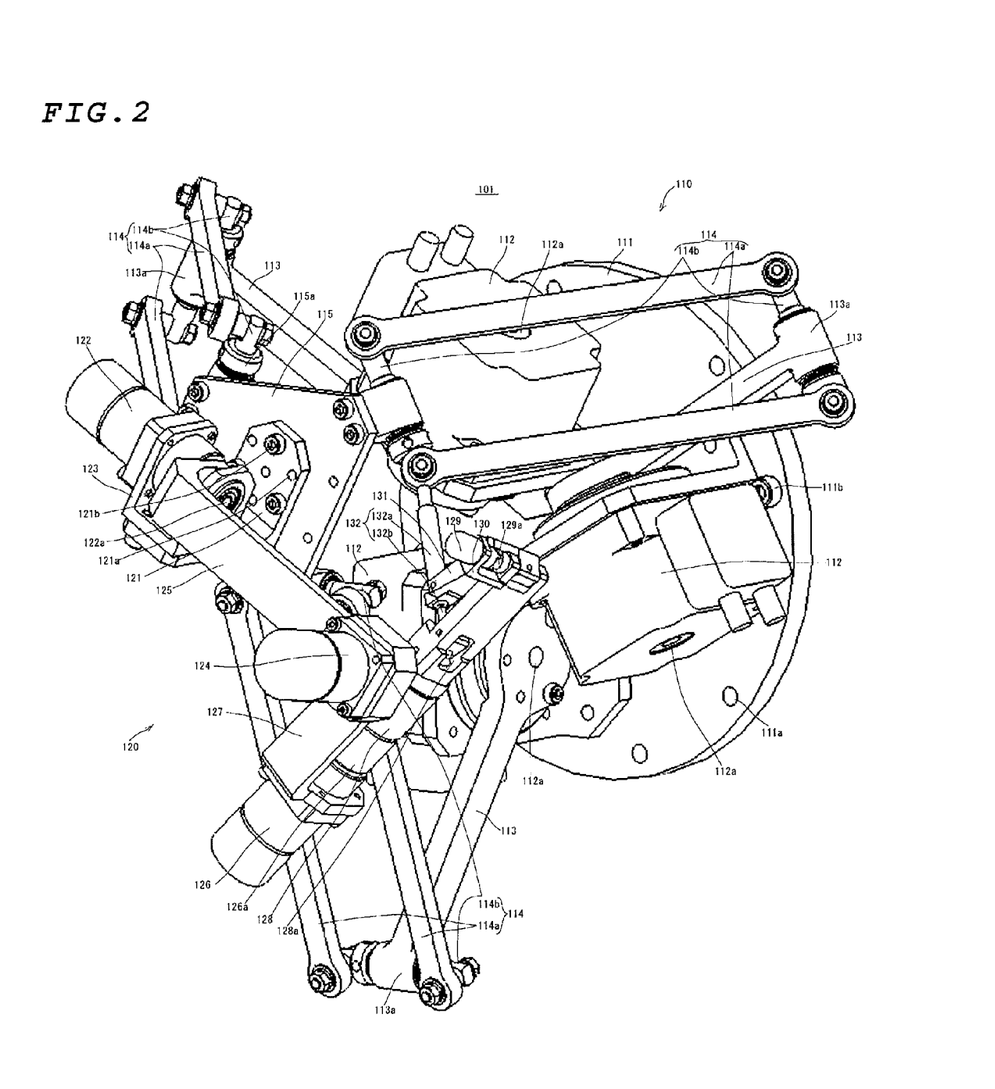
FIG. 2 is a perspective view showing the exterior of the master manipulator shown in FIG. 1.
Figure 3:
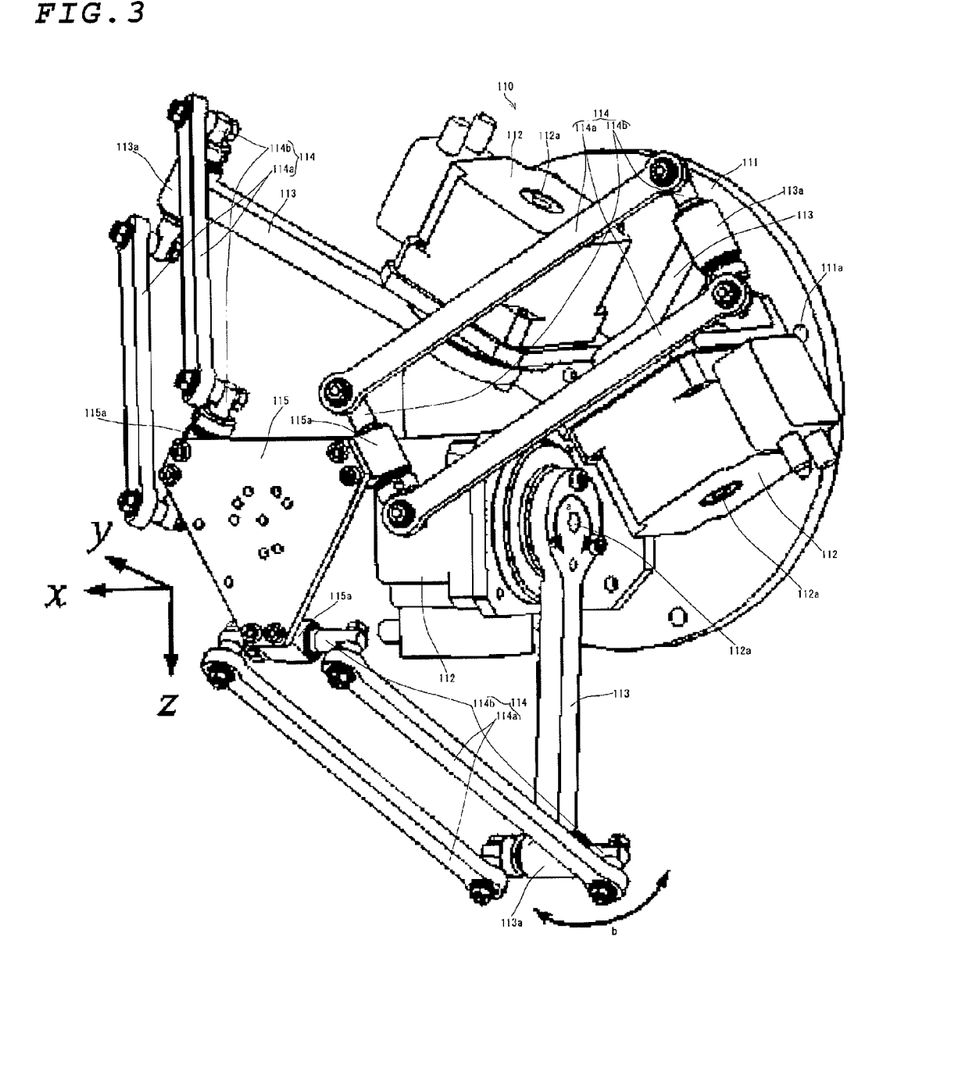
FIG. 3 is a perspective view showing the translation unit shown in FIG. 2.
Figure 4:
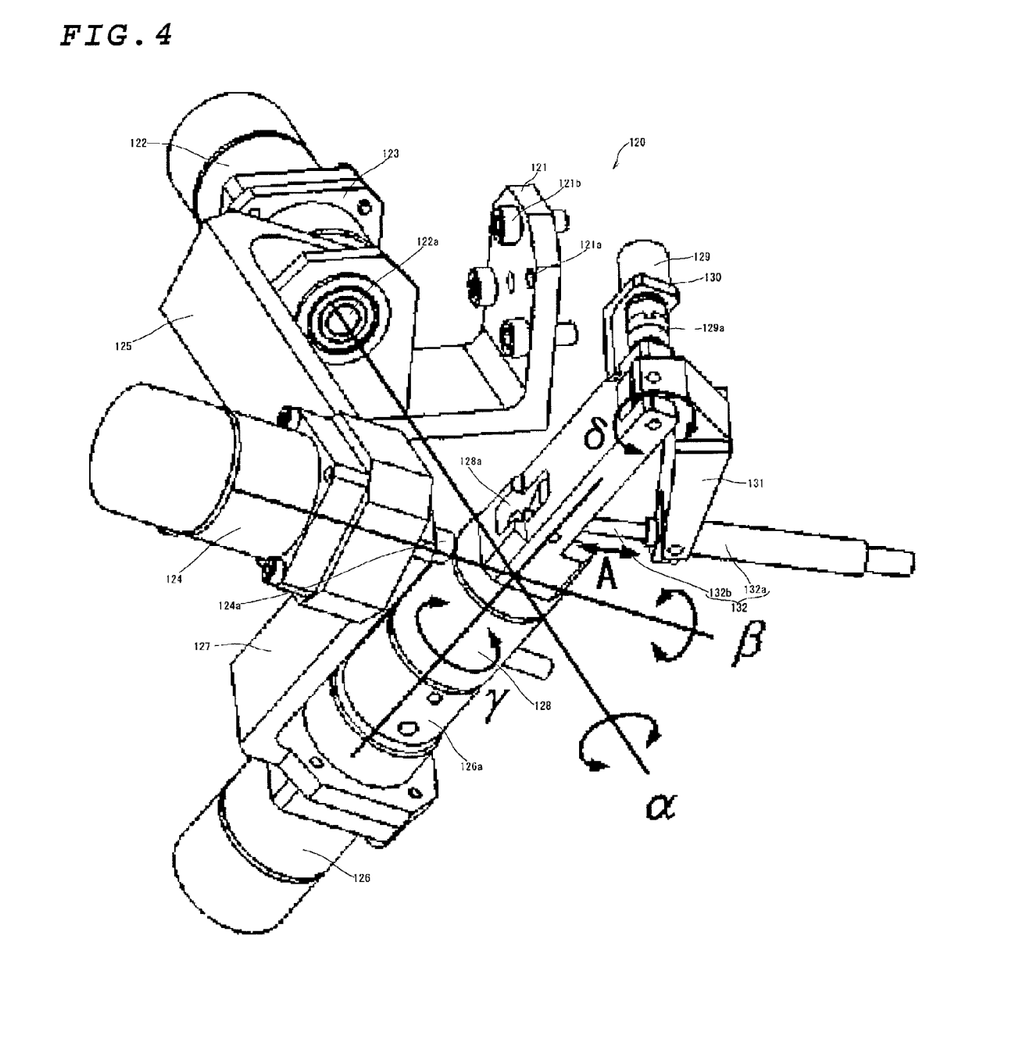
FIG. 4 is a perspective view showing the orientation unit shown in FIG. 2.

FIG. 2 is a perspective view showing the exterior of the master manipulator 101. FIG. 3 is a perspective view showing the translation unit 110. FIG. 4 is a perspective view showing the orientation unit 120. In the master manipulator 101, as shown in FIG. 2, the orientation unit 120 is fixed to the translation unit 110 with screws, which is in turn fixed to, for example, a housing (not shown) with screws. The master manipulator 101 is similar to the slave manipulator 105 in that the number of degrees of freedom is seven, but differs from the slave manipulator 105 in that the master manipulator 101 uses a parallel link mechanism and has a compact structure.

The translation unit 110 includes a circular mounting plate 111, three motors 112, three links 113, three sets of parallel links 114, and a triangular fixture plate 115 as shown in FIGS. 2 and 3. The mounting plate 111 has a plurality of through holes 111a drilled in the vicinity of the outer circumferential edge at uniform angular intervals, and screws 111b are inserted into the through holes 111a to fix the mounting plate 111, for example, to a housing. The three motors 112 are disposed on the mounting plate 111 and fixed thereto with screws at uniform angular intervals (120 degrees) along a circumferential line inside the outer circumferential edge in such a way that each of the motor shafts 112a is oriented along a tangential line of the mounting circumferential line. Each of the motors 112 is an AC servo motor with a harmonic gear transmission and an encoder built therein.

The link 113 is assembled in such a way that one end (rear end) thereof is fixed to the motor shaft 112a and the other end (front end) is supported by a bearing 113a in such a way that the bearing 113a becomes perpendicular to the axis of the link. The parallel link 114 includes two links 114a and two link shafts 114b, and adjacent ends of the two links 114a are rotatably supported at both ends of the two link shaft 114b in such a way that the two links 114a can be translated with a predetermined distance maintained therebetween. One of the link shafts 114b fits in the bearing 113a attached to the tip of the link 113. The fixture plate 115 is fixed in such a way that a bearing 115a disposed at each apex of the triangle is oriented parallel to the axis of the beating 113a attached to the link 113. The other link shaft 114b fits in the bearing 115a fixed to each apex of the fixture plate 115.

The thus configured translation unit 110 is a delta mechanism having three degrees of freedom in total, that is, having the link 113 being rotatable around the motor shaft 112a of the motor 112 in the direction indicated by the arrow "a" in FIG. 3, the parallel link 114 being rotatable around the tip of the link 113 in the same direction as the rotational direction "a" of the link 113 and in the direction perpendicular thereto indicated by the arrow "b" in FIG. 3, and the fixture plate 115 being rotatable around the tip of the parallel link 114 in the same direction as the rotational direction "a" of the link 113. The translation unit 110 is therefore characterized in that it produces a large translation force and maintains the same orientation independent of its position.

The orientation unit 120 includes, as shown in FIGS. 2 and 4, an attachment plate 121 that is L-shaped in the side view, a first motor 122, a first motor fixture plate 123 that is U-shaped in the side view, a second motor 124, a second motor fixture plate 125 that is L-shaped in the side view, a third motor 126, a third motor fixture plate 127 that is L-shaped in the side view, a cylindrical rotating arm 128, a force sensor 129, a force sensor fixture plate 130 that is L-shaped in the side view, a rectangular column-like manipulation finger support arm 131, and a rod-like manipulation finger 132. The attachment plate 121 has a plurality of through holes 121a drilled in one end thereof, and screws 121b are inserted into the through holes 121a to fix the attachment plate 121 to the fixture plate 115. The first motor fixture plate 123, to which the first motor 122 is fixed with screws, is fixed to the other end of the attachment plate 121 with screws in such a way that the motor shaft 122a is oriented parallel to the fixture plate 115.

One end of the second motor fixture plate 125 is fixed to the motor shaft 122a of the first motor 122, and the second motor 124 is fixed to the other end of the second motor fixture plate 125 with screws in such a way that the motor shaft 124a is oriented perpendicular to the motor shaft 122a of the first motor 122. One end of the third motor fixture plate 127 is fixed to the motor shaft 124a of the second motor 124, and the third motor 126 is fixed to the other end of the third motor fixture plate 127 with screws in such a way that the motor shaft 126a is oriented perpendicular to the motor shaft 122a of the first motor 122 and the motor shaft 124a of the second motor 124. The rear end of the rotating arm 128 is connected and fixed to the motor shaft 126a of the third motor 126 in such a way that the axial direction of the rotating arm 128 is oriented in the axial direction of the motor shaft 126a of the third motor 126.

The force sensor 129 is fixed to the tip of the rotating arm 128 via the force sensor fixture plate 130 in such a way that the rotating shaft 129a of the force sensor 129 is oriented perpendicular to the motor shaft 126a of the third motor 126. The manipulation finger support arm 131 is supported at the tip of the rotating arm 128 in such a way that the rear end of the manipulation finger support arm 131 is rotatable around the rotating shaft 129a of the force sensor 129. The manipulation finger 132 includes a hollow cylindrical body 132a and a solid cylindrical slider 132b that is inserted through the body 132a and slidable in the axial direction. The tip of the body 132a is rotatably supported at the tip of the manipulation finger support arm 131 in the same direction as the rotating shaft 129a of the force sensor 129. The tip of the slider 132b is inserted and secured in a hole 128a drilled in a substantially central area of the rotating arm 128. Each of the first motor 122, the second motor 124, and the third motor 126 is an AC servo motor with a harmonic gear transmission and an encoder built therein. The force sensor 129 is a six-axis force sensor capable of detecting translational forces in three axial directions perpendicular to one another and moments around the three axes.

The thus configured orientation unit 120 is a serial gimbal mechanism having four degrees of freedom in total, that is, having the second motor fixture plate 125 being rotatable around the motor shaft 122a of the first motor 122 in the direction α in FIG. 4, the third motor fixture plate 127 being rotatable around the motor shaft 124a of the second motor 124 in the direction β in FIG. 4, the rotating arm 128 being rotatable around the motor shaft 126a of the third motor 126 in the direction γ in FIG. 4, the manipulation finger support arm 131 being rotatable around the rotating shaft 129a of the force sensor 129 in the direction δ in FIG. 4, and the body 132a of the manipulation finger 132 being slidable in the axial direction (the direction A in FIG. 4) along the slider 132b when operated by the operator. The orientation unit 120 is therefore characterized by its broad movable range that covers the motion of the human hand.

Figure 5:
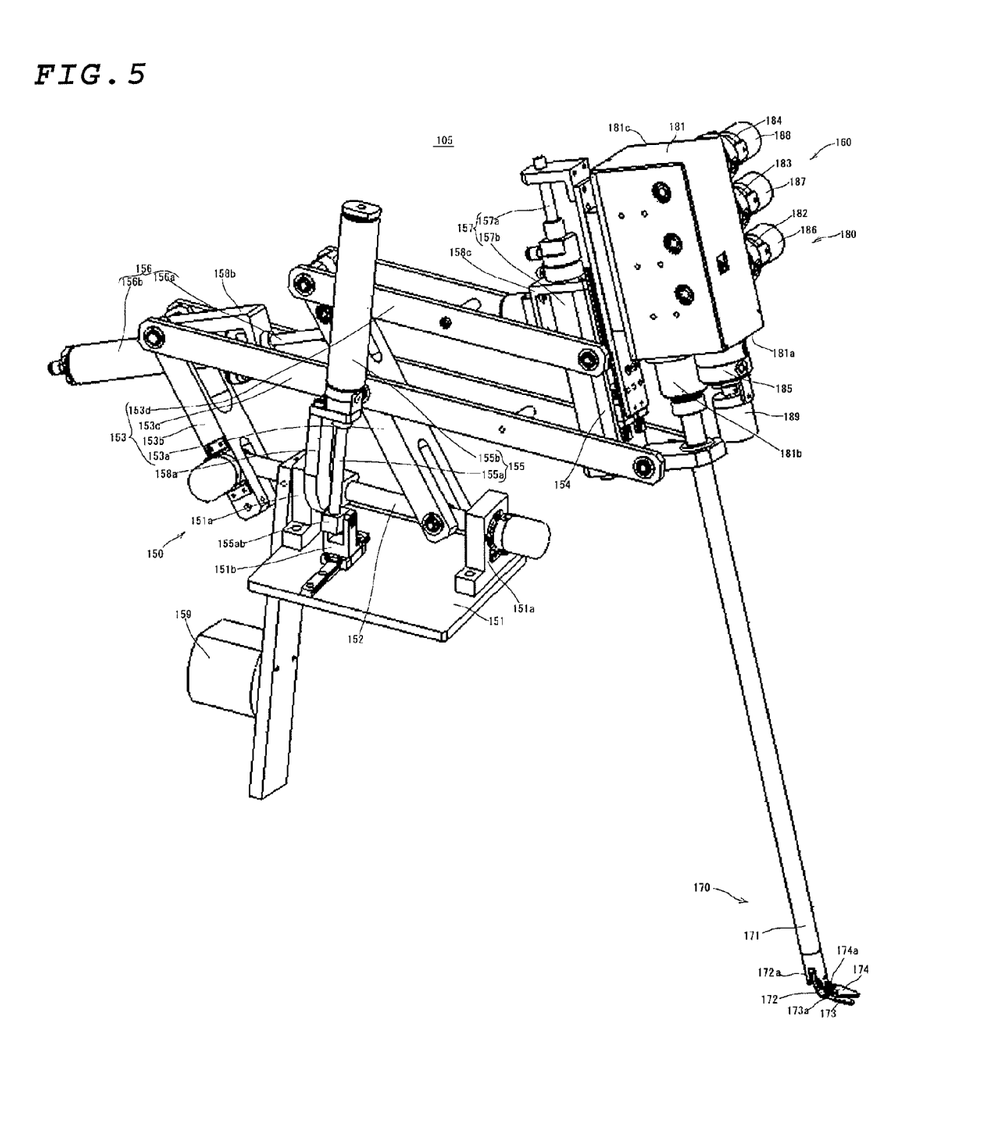
FIG. 5 is a perspective view showing the exterior of the slave manipulator shown in FIG. 1.
Figure 6:
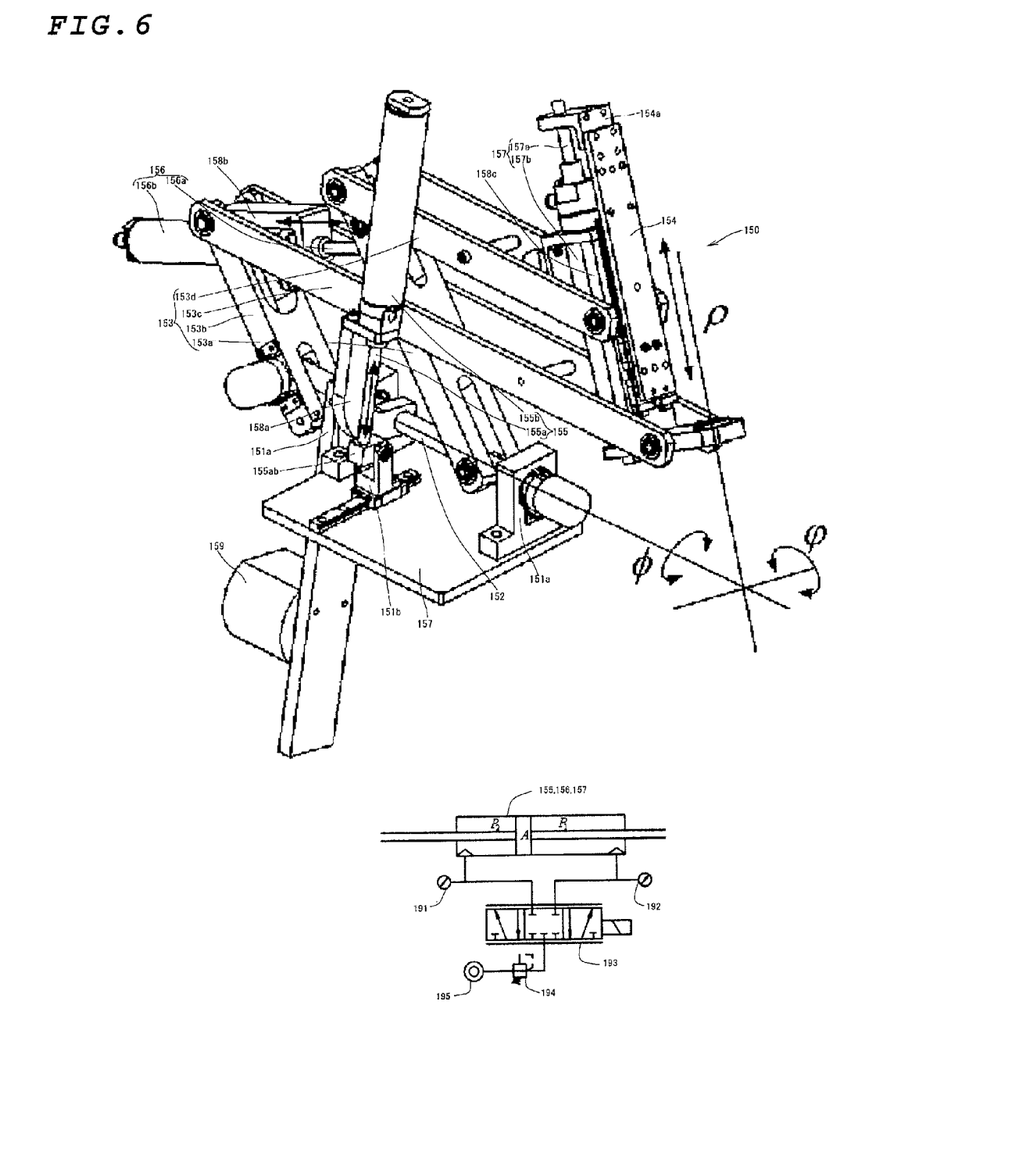
FIG. 6 is a perspective view showing the holding unit shown in FIG. 5 and also shows a pneumatic circuit for driving a pneumatic cylinder.
Figure 7:
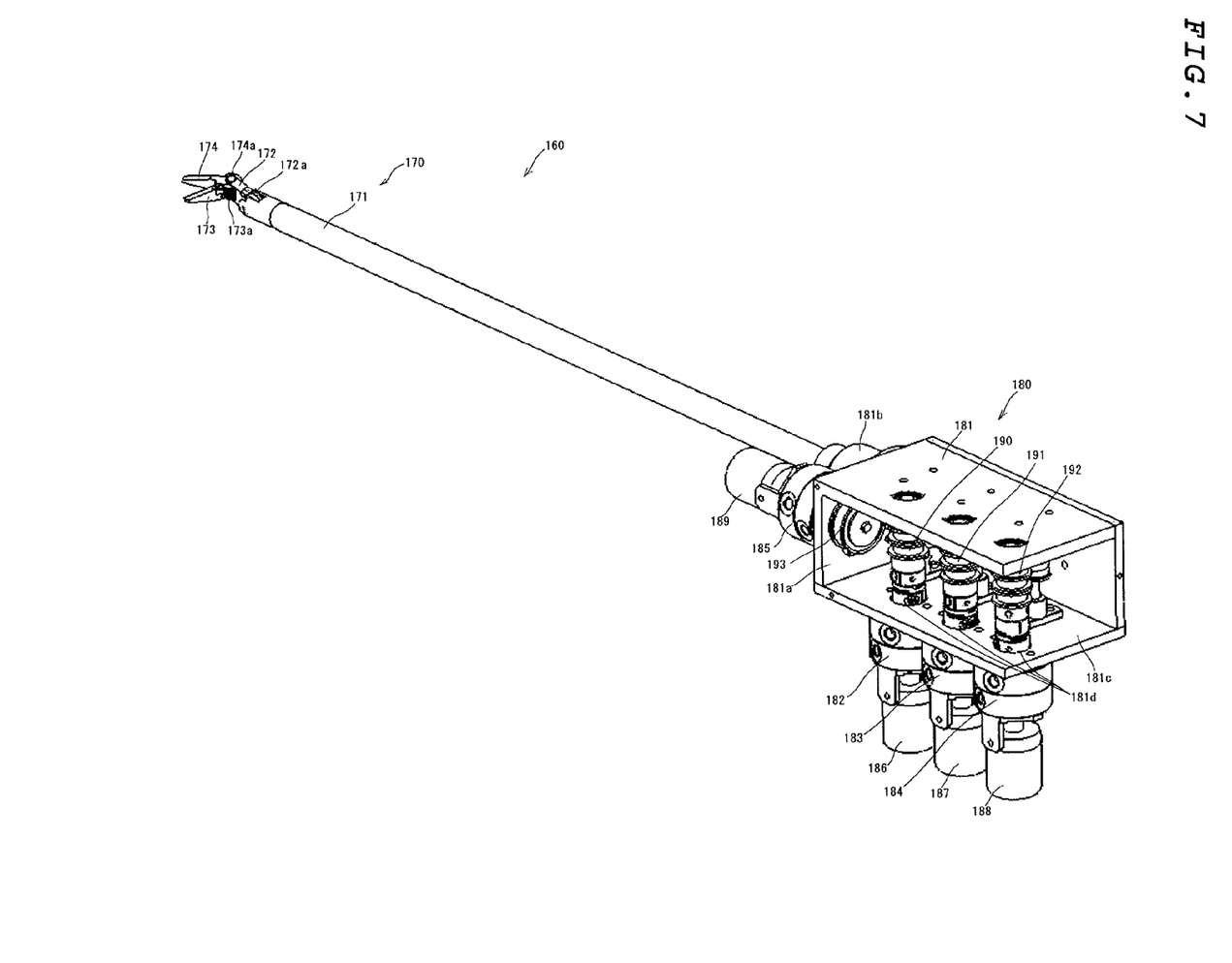
FIG. 7 is a perspective view showing the grip unit shown in FIG. 5.

FIG. 5 is a perspective view showing the exterior of the slave manipulator 105. FIG. 6 is a perspective view showing the holding unit 150. FIG. 7 is a perspective view showing the grip unit 160. In the slave manipulator 105, as shown in FIG. 5, the grip unit 160 is fixed to the holding unit 150 with screws, which is in turn fixed to, for example, a housing (not shown) with screws. The slave manipulator 105 is similar to the master manipulator 101 in that the number of degrees of freedom is seven, but differs from the master manipulator 101 in that the slave manipulator 105 uses a combination of two sets of parallel link mechanisms and a gimbal mechanism as well as a wire mechanism and has a compact structure.

As shown in FIGS. 5 and 6, the holding unit 150 includes a rectangular base plate 151, a parallel link support shaft 152, two sets of parallel links 153, a grip unit support base 154, three pneumatic cylinders (pneumatic actuators) 155, 156, and 157, and three cylinder fixture plates 158a, 158b, and 158c. Two bearings 151a are disposed on and fixed to the base plate 151 with a predetermined distance therebetween. The two bearings 151a rotatably support the parallel link support shaft 152. A rod support 151b, which rotatably supports a block 155ab fixed to the tip of the rod 155a of the first pneumatic cylinder 155, is also disposed on and fixed to the base plate 151 between the bearings 151a. The body 155b of the first pneumatic cylinder 155 is supported by one end of the cylinder fixture plate 158a, which is L-shaped in the side view, and the other end thereof is fixed to a substantially central portion of the parallel link support shaft 152.

One end of each of two links 153a and 153b, which form one of the parallel links 153, is rotatably supported at the corresponding end of the parallel link support shaft 152. With the two links 153a and 153b held parallel to each other, one end of a link 153c, which is part of the other parallel link 153, is rotatably supported at the other end of the link 153b, and a substantially central portion of the link 153c is rotatably supported at a substantially central portion of the link 153a. One end of a link 153d, which is part of the other parallel link 153, is rotatably supported at the other end of the link 153a. With the two links 153c and 153d held parallel to each other, the other ends of the links 153c and 153d are rotatably supported by the cylinder fixture plate 151.

The body 156b of the second pneumatic cylinder 156 is supported by one end of the cylinder fixture plate 158b, which is L-shaped in the side view, and the other end thereof is rotatably supported at the portion where the links 153b and 153c are rotatably supported. A block (not shown) fixed to the tip of the rod 156a of the second pneumatic cylinder 156 is rotatably supported between the two ends of the link 153a. The body 157b of the third pneumatic cylinder 157 is supported by one end of the cylinder fixture plate 158c, which is L-shaped in the side view, and the grip unit support base 154 is attached to the cylinder fixture plate 158c in a slidable manner in the direction in which the rod 157a of the third pneumatic cylinder 157 moves. The tip of the rod 157a of the third pneumatic cylinder 157 is fixed to a fixture plate 154a fixed to the upper portion of the grip unit support base 154. Each of the pneumatic cylinders 155, 156, and 157 is a low-friction single rod double acting cylinder.

As shown in FIG. 6, both chambers of each of the pneumatic cylinders 155, 156, and 157 are connected respective control ports of a five-port, flow-control servo valve 193 (five ports in total: one supply port, two control ports, and two exhaust ports). A control signal is used to adjust the opening of one of the control ports of the servo valve 193, and hence adjust the flow from the supply port into one of the chambers of each of the pneumatic cylinders 155, 156, and 157. At the same time, the air in the other chamber is released from the other control port through the corresponding exhaust port to the atmosphere. The pressure difference between both chambers of each of the pneumatic cylinders is thus controlled.

The thus configured holding unit 150 is a combination of a parallel link mechanism and a gimbal mechanism, the parallel link mechanism having three degrees of freedom in total, that is, having the parallel links 153 being rotatable around the parallel link support shaft 152 in the direction φ in FIG. 6 in response to the motion of the first pneumatic cylinder 155 and being rotatable in the direction φ in FIG. 6 around the portions where the parallel link support shaft 152 and the links 153a and 153b are rotatably supported in response to the motion of the second pneumatic cylinder 156, and the grip unit support base 154 being slidable in the direction ρ in FIG. 6 in response to the motion of the third pneumatic cylinder 157. The holding unit 150 can therefore be designed in such a way that the trocar, which is set in the abdomen of the subject during laparoscopic surgery, is a stationary point. The holding unit is thus characterized in that it is not necessary to directly support the forceps at the hole into which the forceps are inserted, so that the holding unit 150 can be operated with minimal burden on the body at the hole into which the forceps are inserted, and the position coordinates of the port of the trocar are not required in the kinetics computation. Further, a counterweight 159 is used to mechanically compensate part of the self-weight of the holding unit 150.

Figure 8:
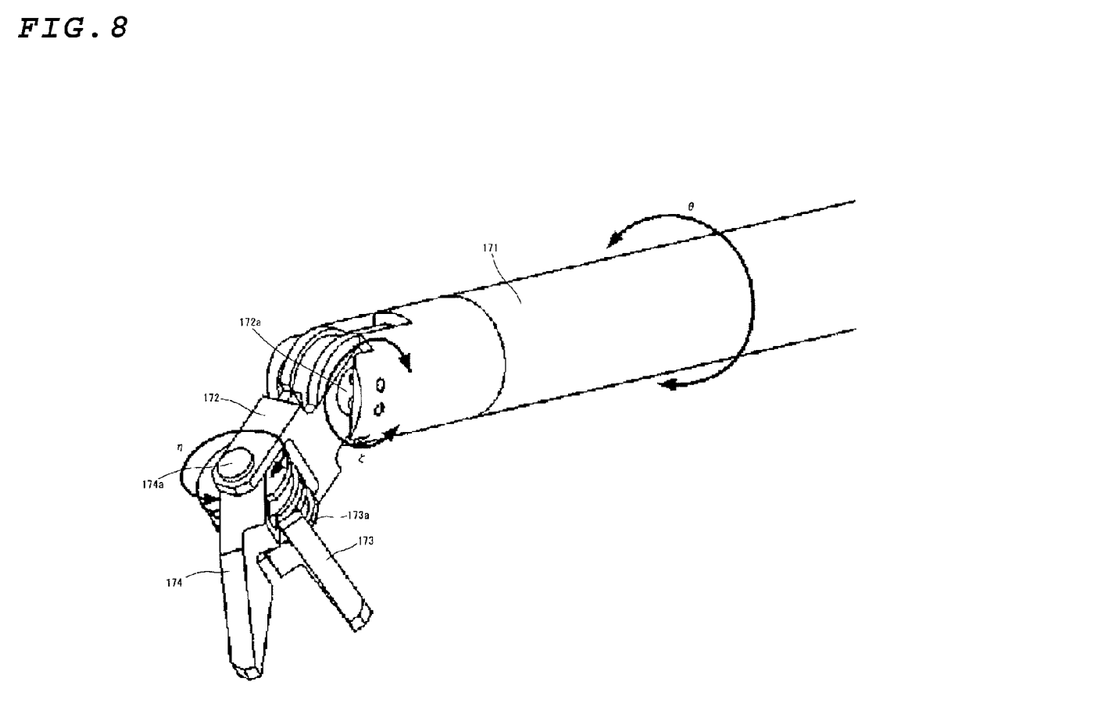
FIG. 8 is a perspective view showing the forceps showing in FIG. 7.
Figure 9:
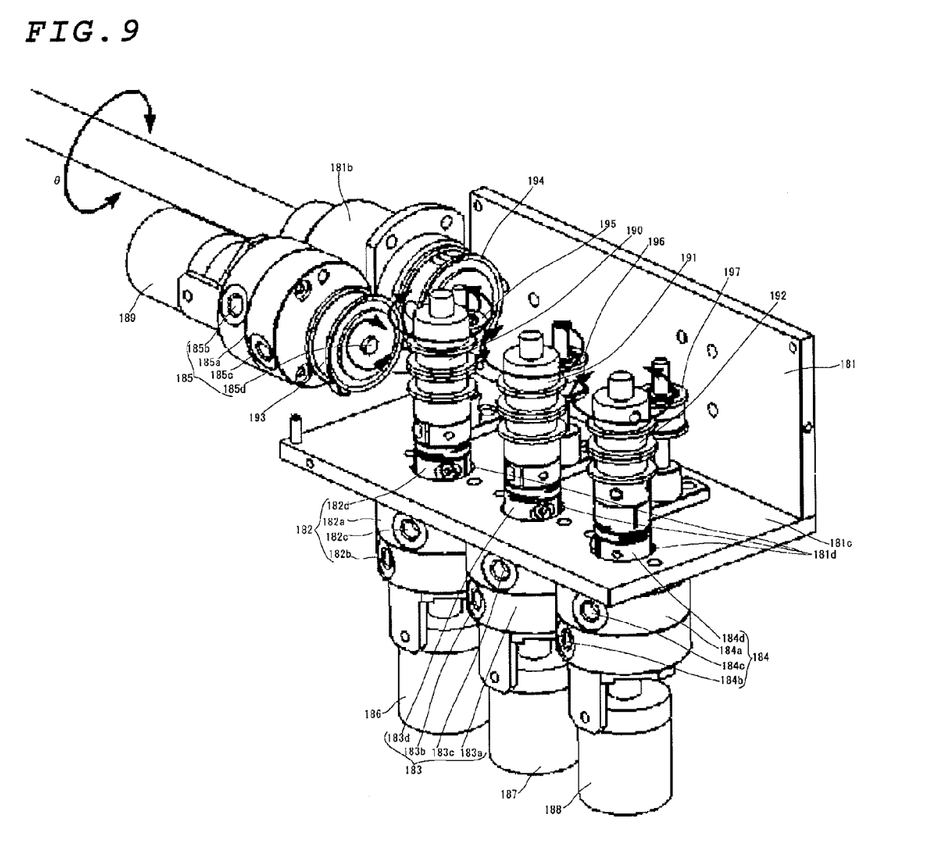
FIG. 9 is, a perspective view showing the forceps holding unit shown in FIG. 7.

The grip unit 160, which includes forceps 170 and a forceps holding unit 180 as shown in FIGS. 5 and 7, is now described also with reference to FIG. 8, a perspective view showing the forceps 170, and FIG. 9, a perspective view showing the forceps holding unit 180. The forceps 170 includes a rod-like forceps shaft 171, a forceps finger holder 172, and two forceps fingers 173 and 174. The rear end of the forceps shaft 171 is rotatably supported by the forceps holding unit 180. One end of the forceps finger holder 172 is rotatably supported at the tip of the forceps shaft 171 around a rotating shaft 172a disposed in a direction perpendicular to the axis of rotation of the forceps shaft 171. One end of each of the forceps fingers 173 and 174 is rotatably supported at the other end of the forceps finger holder 172 around rotating shafts 173a and 174a disposed in a direction perpendicular to the axis of rotation of the forceps shaft 171 and the rotating shaft 172a of the forceps finger holder 172.

The forceps holding unit 180 includes a box-like holding body 181, four pneumatic rotary actuators (pneumatic actuators) 182, 183, 184, and 185, four sets of rotary encoders and pressure sensors 186, 187, 188, and 189, four drive pulleys 190, 191, 192, and 193, one driven pulley 194, and three direction conversion pulleys 195, 196, and 197. The holding body 181 is fixed to the grip unit support base 154 in the grip unit 150 with screws. The forceps shaft 171 is inserted through and rotatably supported by a bearing 181b attached to a side 181a of the holding body 181 in such a way that the bearing 181b covers a hole provided in the side 181a, and the driven pulley 194 is attached to the rear end of the forceps shaft 171.

The first to fourth pneumatic rotary actuators 182, 183, 184, and 185 include cylindrical bodies 182a, 183a, 184a, and 185a. Each of the bodies includes a swinging piece (not shown) having a shaft that is located at the center of the body and can swing within a predetermined angular range, the swinging piece extending from the swinging shaft to the inner circumferential surface of the body, and a partition plate (not shown) extending from the swinging shaft to the inner circumferential surface of the body. By supplying and exhausting air through two kinds of ports, air supply/exhaust ports 182b/182c (183b/183c, 184b/184c, 185b/185c) provided in the circumferential surface of the body 182a (183a, 184a, 185a), to and from the two chambers partitioned by the swinging piece and the partition plate so as to swing the swinging plate, a rotating shaft 182d (183d, 184d, 185d) connected to the swinging shaft is rotated within a predetermined angular range.

The first to third pneumatic rotary actuators 182, 183, and 184, to which the first to third rotary encoders and pressure sensors 186, 187, and 188 are connected, are attached in line to a side 181c, which is disposed perpendicular to the side 181a of the holding body 181, in such a way that the rotating shafts 182d, 183d, and 184d pass through three holes 181d arranged in line in the side 181c, and the first to third drive pulleys 190, 191, and 192 are disposed in line and attached to the tips of the rotating shafts 182d, 183d, and 184d. The first to third direction conversion pulleys 195, 196, and 197 are disposed inside the side 181c and rotatably supported next to the first to third drive pulleys 190, 191, and 192, respectively. Three loop wires (not shown) run from the first to third drive pulleys 190, 191, and 192 via the first to third direction conversion pulleys 195, 196, and 197 to the rotating shaft 172a of the forceps finger holder 172 and the rotating shafts 173a and 174a of the two forceps fingers 173 and 174, respectively. The three loop wires thus engage the first to third drive pulleys 190, 191, and 192 as well as the rotating shaft 172a of the forceps finger holder 172 and the rotating shafts 173a and 174a of the two forceps fingers 173 and 174, respectively.

The fourth swing pneumatic actuator 185, to which the fourth rotary encoder and pressure sensor 189 is connected, is attached to the side 181a in such a way that the rotating shaft 185d is oriented parallel to the forceps shaft 171 and passes through a hole provided in the side 181a of the holding body 181, and the fourth drive pulley 193 is disposed next to the driven pulley 194 and attached to the tip of the rotating shaft 185d. A loop wire (not shown) engages the fourth drive pulley 193 and the driven pulley 194 so that the loop wire runs between the fourth drive pulley 193 and the driven pulley 194.

The thus configured grip unit 160 is a 4-DOF wire mechanism for bending, gripping, and rotating, that is, having the forceps finger holder 172 being rotatable around the rotating shaft 172a in the direction ζ in FIG. 8 in response to the motion of the first pneumatic rotary actuator 182, the two forceps fingers 173 and 174 being rotatable around the rotating shafts 173a and 174a in the direction η in FIG. 8 in response to the motions of the second and third pneumatic rotary actuators 183 and 184, and the forceps shaft 171 being rotatable around the rotating shaft 185d in the direction θ in FIGS. 8 and 9 in response to the motion of the fourth pneumatic rotary actuator 185. The forceps 170 and the forceps holding unit 180 are therefore characterized in that they are separable from each other in consideration of the disinfection process.

Figure 10:
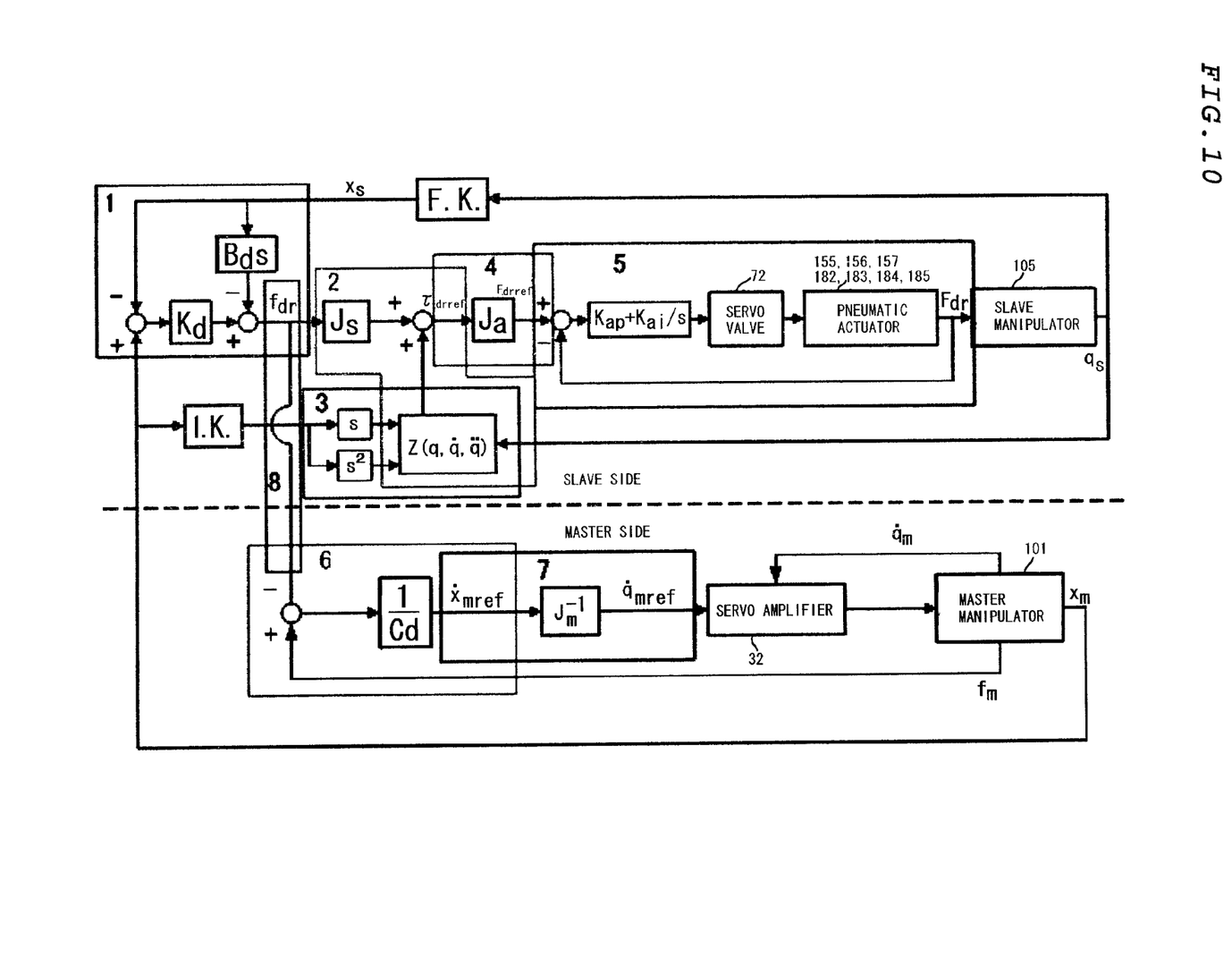
FIG. 10 is a control block diagram of the multi-DOF forceps system.

FIG. 10 is a control block diagram of the multi-DOF forceps system 100. A 5-port spool servo valve 172 is used to drive the pneumatic cylinders 155, 156, and 157 and the pneumatic rotary actuators 182, 183, 184, and 185. It is also possible to apply a control method in which a disturbance observer uses the drive force Fdr of each of the pneumatic cylinders 155, 156, and 157 as well as the pneumatic rotary actuators 182, 183, 184, and 185, all of which are pneumatic actuators, (the drive force Fdr is calculated using the pressure difference between the chambers) to estimate an external force flex acting on the forceps fingers 173 and 174, which form the tip of the slave manipulator 105. However, the use of this control method requires an inverse dynamics model of the whole portion including the pneumatic cylinders 155, 156, and 157, the pneumatic rotary actuators 182, 183, 184, and 185, and the forceps fingers 173 and 174. However, since wires are used for power transmission, the modeling is not easy due to friction of the wires and interference among the degrees of freedom. To derive such a model, a neural network is used to learn a given arbitrary drive pattern.

In general, the response in a master-slave system will be ideal when the position and the force of the master manipulator are the same as those of the slave manipulator. However, even when such an ideal response is achieved, and hence the operator feels as if he/she were directly doing operation with his/her own hands, the performance of the operation totally depends on the operator. To address such a problem, a bilateral control system is used, in which impedance control applied to the master manipulator 101 differs from that applied to the slave manipulator 105.

The slave controller 107 makes use of the softness of the pneumatic cylinders 155, 156, and 157 and the pneumatic rotary actuators 182, 183, 184, and 185 to apply a control method in which compliance is imparted to the slave manipulator 105. That is, since air can be compressed, the slave manipulator 105 has softness. Further, such softness is adjustable by adjusting the pressure of the compressed air.

The compliance of the slave manipulator 105 can prevent generation of an excessive force. The softness of the slave manipulator 105 provides a shock absorbing effect when the slave manipulator 105 hits an object hard.

In this case, when the slave manipulator 105 comes into contact with a highly rigid environment, the deviation of the position of the master manipulator 101 from that of the slave manipulator 105 increases due to the compliance. Even when the position of the master manipulator 101 deviates from that of the slave manipulator 105, the operator can work normally because the slave manipulator 105, which is used for surgery, primarily comes into contact with an organ and the operator works on the organ while looking at images of the slave manipulator 105 through an endoscope.

On the other hand, the master manipulator 101 desirably operates in a stably manner by imparting a moderate viscous effect. To this end, the master controller 103 employs a position-based impedance control method (admittance control method) in which a force control loop includes a motion control loop in consideration of the characteristics of the motors 112, the first motor 122, the second motor 124, and the third motor 126. The slave controller 107 employs a force-based impedance control method in which a motion control loop includes a force control loop because the pneumatic cylinders 155, 156, and 157 and the pneumatic rotary actuators 182, 183, 184, and 185 are characterized by high back-drivability and low stiffness.

As shown in FIG. 10, the master controller 103 and the slave controller 107 control the master manipulator 101 and the slave manipulator 105, respectively, in such a way that the manipulators have the following impedance characteristics.

For the slave manipulator 105, $$-fs = Kd(xs-xm) + Bd\, dxs/dt \quad (1)$$

For the master manipulator 101, $$fm - fs = Cd\, dxm/dt \quad (2)$$

In the above equations,
xs: the position and orientation of the tip (forceps fingers 173 and 174) of the slave manipulator 105
xm: the position and orientation of the tip (manipulation finger 132) of the master manipulator 101
fs: the force that the tip of the slave manipulator 105 applies to the outer environment
fm: the force that the operator applies to the tip of the master manipulator 101
Kd: the set stiffness of the slave manipulator 105
Bd: the set viscosity of the slave manipulator 105
Cd: the set viscosity of the master manipulator 101

To achieve the equation (1), impedance control including a force control loop is applied to the slave manipulator 105. The equation of motion of the slave manipulator 105 is expressed in the joint coordinate system as follows:

$$\tau dr - Js(\text{transposition}) fs = Z(qs, dqs/dt, d^2qs/dt^2) \quad (3)$$

In the above equation,
τdr: the drive torque at each joint of the slave manipulator 105
Z: the inverse dynamics function for the slave manipulator 105
qs: the displacement of each joint of the slave manipulator 105
Js: the Jacobi matrix representing the transition from the displacements of the joints to the displacement of the tip position of the slave manipulator 105

To achieve the equation (1), the force fdr that the tip of the slave manipulator 105 should produce and the target value τdrref of the drive torque of each of the pneumatic cylinders 155, 156, and 157 and the pneumatic rotary actuators 182, 183, 184, and 185 are calculated as follows:

$$fdr = Kd(xs-xm) + Bd\, dxs/dt \quad (4)$$

(in the frame 1 in FIG. 10)

$$\tau dr\text{ref} = -Js(\text{transposition}) fdr + Z(qs, dqs/dt, d^2qs/dt^2) \quad (5)$$

(in the frame 2 in FIG. 10)

Assuming that the dynamic characteristics of the pneumatic cylinders 155, 156, and 157 and the pneumatic rotary actuators 182, 183, 184, and 185 are satisfactory so that τdrref coincides with τdr, the equation (4) is substituted into the equation (5), which is then substituted into the equation (3) to derive the equation (1). In practice, to prevent the equation (5) from being unstable due to phase retardation, the speed and acceleration among the inputs in the inverse dynamics model are determined from a target value of the trajectory of the master manipulator 101 (in the frame 3 in FIG. 10). To produce the torque calculated by using the equation (5) at each joint, mechanics computation is used to convert the torque into the drive force target value Fdrref of each of the pneumatic cylinders 155, 156, and 157 and the pneumatic rotary actuators 182, 183, 184, and 185.

$$Fdr\text{ref} = Ja \tau dr\text{ref} \quad (6)$$

(in the frame 4 in FIG. 10)
In the above equation,
Ja: Jacobian representing the transition from the displacements of the pneumatic cylinders 155, 156, and 157 and the pneumatic rotary actuators 182, 183, 184, and 185 to the displacements of the joint Then, PI control is carried out to produce the drive force calculated by using the equation (6).

$$u = (Kap + Kai/s) \cdot (Fdr\text{ref} - Fdr) \quad (7)$$

in the frame 5 in FIG. 10)
In the above equation,
u: the control voltage for the servo valve 172
Kap: proportional gain
Kai: integral gain
Fdr: the drive forces of the pneumatic cylinders 155, 156, and 157 and the pneumatic rotary actuators 182, 183, 184, and 185 calculated from pressure values Admittance control is applied to the master manipulator 101 to achieve the equation (2).

$$dxm/dt = (fm - fs)/Cd \quad (8)$$

(in the frame 6 in FIG. 10) dqm/dt = Jm(inverse)dxm/dt (in the frame 7 in FIG. 10)

As seen from the equation (8), the contact force between the slave manipulator 105 and the external environment is required. When the impedance control is applied to the slave manipulator 105, fdr coincides with fs, so that fdr is supplied as an estimated value to the master controller 103 and the slave controller 107 (in the frame 8 in FIG. 10). The target drive force value Fdrref of each of the pneumatic cylinders 155, 156, and 157 and the pneumatic rotary actuators 182, 183, 184, and 185 can be produced in a quick and precise manner by the differential pressure control loop in each of the cylinders and actuators. It is therefore possible to compensate the characteristics disadvantageously affecting the positioning, such as air compression properties and a deviation of the neutral point of the valve.

As described above, according to the multi-DOF forceps system 100 of this embodiment, the force acting on the slave manipulator 105 is fed back to the master manipulator 101 by operating the master manipulator 101 primarily under electrically-driven speed control and the slave manipulator 105 primarily under pneumatically-driven force control. Therefore, in the master manipulator 101, it is not necessary to compensate for the dynamics and the self-weight of the master manipulator 101 in the motion range of the operator, allowing highly accurate, broadband positional control, which is specific to an electrically-driven system, and in the slave manipulator 105, nonlinearity characteristics specific to a pneumatically-driven system presents passive softness, provides a high mass-to-output ratio, and produces a large force. Further, the slave manipulator 105, which is configured as a pneumatically-driven system, can be installed in an apparatus involving a magnetic field, for example, an MRI (Magnetic Resonance Imaging), and used in surgery.

Since the master manipulator 101 includes the 3-DOF translation unit 110 and the 4-DOF orientation unit 120 connected to the translation unit 110, and the slave manipulator 105 includes the 3-DOF holding unit 150 and the 4-DOF grip unit 160 held by the holding unit 150, the motion of the human hand on the master manipulator 101 side can be reproduced on the slave manipulator 105 side. Since the translation unit 110, the orientation unit 120, the holding unit 150, and the grip unit 160 are configured as the delta mechanism, the gimbal mechanism, the combination of the parallel link mechanism and the gimbal mechanism, and the wire mechanism, respectively, the master manipulator 101 and the slave manipulator 105 are configured differently from each other and the shapes thereof can be optimized in terms of operability. Since the grip unit 160 includes pneumatic rotary actuators 182, 183, 184, and 185 and wires connected to the pneumatic rotary actuators 182, 183, 184, and 185, and the grip unit 160 is driven by pulling motions of the wires in response to the motions of the pneumatic rotary actuators 182, 183, 184, and 185, the grip unit 160 can directly transmit the swing motions of the pneumatic rotary actuators 182, 183, 184, and 185. Such a configuration allows reduction in weight of the slave manipulator 105.

Further, since the force acting on the grip unit 160 is estimated from the drive forces of the pneumatic cylinders 155, 156, and 157 and the pneumatic rotary actuators 182, 183, 184, and 185 by making use of the back drivability thereof, no force sensor is required on the grip unit 160, thereby providing advantages of reducing the size of the grip unit 160, making disinfection of the grip unit 160 easy, and eliminating the need for calibration of the grip unit 160. Moreover, since the compliance-based control is applied to the slave manipulator 105, the slave manipulator 105 will not produce an excessive force.

Since the position-based impedance control in which a force control loop includes a motion control loop is applied to the master manipulator 101, and the force-based impedance control in which a motion control loop includes a force control loop is applied to the slave manipulator 105, the slave manipulator 105 can be stably operated by imparting a moderate viscosity effect to the master manipulator 101. That is, the control system according to this embodiment allows the operator to feel as if he/she pushes and pulls the master manipulator 101 fixed to a stationary wall via a damper. It is also possible to connect the master manipulator 101 to the slave manipulator 105 via a spring and a damper. The values of the spring and the damper are adjustable by selecting the control parameters.

In the embodiment described above, although the multi-DOF forceps system 100 remotely controllable by means of wired communication has been described, the multi-DOF forceps system 100 may be a system using wireless communication or a system that is controllable from a nearby location. Further, although the multi-DOF forceps system 100 has been described as an endoscopic surgery-assisting apparatus, the multi-DOF forceps system 100 can be configured as an apparatus for training a doctor or an apparatus for evaluating skill. Although the invention has been described with reference to the multi-DOF forceps system 100 used in medical fields as a manipulation system having a force feedback capability, the invention is not limited thereto. The invention is generally applicable to various manufacturing fields.

The invention claimed is:

1. A manipulation system having a force feedback capability in which automatic operation of a slave manipulator that follows manual operation of a master manipulator is bilaterally controllable by means of communication, the manipulation system characterized in that the force acting on the slave manipulator is fed back to the master manipulator by operating the master manipulator under electrically-driven speed control and the slave manipulator under pneumatically-driven force control,
the master manipulator includes a 3-DOF translation unit and a 4-DOF orientation unit connected to the translation unit, and the slave manipulator includes a 3-DOF holding unit and a 4-DOF grip unit held by the holding unit.

2. The manipulation system having a force feedback capability according to claim 1, characterized in that the translation unit is a delta mechanism, the orientation unit is a gimbal mechanism, the holding unit is a combination of a parallel link mechanism and a gimbal mechanism and the grip unit is a wire mechanism.

3. The manipulation system having a force feedback capability according to claim 2, characterized in that the grip unit includes pneumatic rotary actuators and wires connected to the pneumatic actuators, and the grip unit is driven by pulling motions of the wires in response to the motions of the pneumatic actuators.

4. The manipulation system having a force feedback capability according to any one of claims 1 to 3, characterized in that compliance-based control is applied to the slave manipulator.

5. The manipulation system having a force feedback capability according to any one of claims 1 to 3, characterized in that position-based impedance control in which a force control loop includes a motion control loop is applied to the master manipulator, and force-based impedance control in which a motion control loop includes a force control loop is applied to the slave manipulator.

6. The manipulation system having a force feedback capability according to any one of claims 1 to 3, characterized in that automatic operation of the slave manipulator that follows manual operation of the master manipulator is bilaterally controlled by means of wired communication.

7. The manipulation system having a force feedback capability according to claim 1, characterized in that the slave manipulator is controlled by means of (1) and (2):
(1) the force fdr that the tip of the slave manipulator should produce is calculated as follows:

$$fdr = Kd(xs-xm) + Bd\, dxs/dt$$

wherein,
Kd: the set stiffness of the slave manipulator
xs: the position and orientation of the tip of the slave manipulator
xm: the position and orientation of the tip of the master manipulator
Bd: the set viscosity of the slave manipulator
(2) the target value Σdrref of the drive torque of the pneumatically-driven system is calculated as follows:

$$\tau drref = -Js(\text{transposition})fdr + Z(qs, dqs/dt, d^2qs/dt^2)$$

wherein,
Js: the Jacobi matrix representing the transition from the displacements of the joints to the displacement of the tip position of the slave manipulator
Z: the inverse dynamics function for the slave manipulator
qs: the displacement of each joint of the slave manipulator
$dqs/dt$, $d^2qs/dt^2$: the speed and acceleration are determined from a target value of the trajectory of the master manipulator.

8. The manipulation system having a force feedback capability according to claim 7, characterized in that the master manipulator is controlled as follows:
dxm/dt is calculated as follows:

$$dxm/dt = (fm-fs)/Cd$$

wherein,
fm: the force that the operator applies to the tip of the master manipulator
fs: fs is determined from the force fdr that the tip of the slave manipulator should produce
Cd: the set viscosity of the master manipulator.

9. The manipulation system having a force feedback capability according to claim 1, characterized in that the slave manipulator is controlled as follows:
the target value Σdrref of the drive torque of the pneumatically-driven system is calculated as follows:

$$\tau drref = -Js(\text{transposition})fdr + Z(qs, dqs/dt, d^2qs/dt^2)$$

wherein,
- Js: the Jacobi matrix representing the transition from the displacements of the joints to the displacement of the tip position of the slave manipulator
- fdr: the force that the tip of the slave manipulator should produce
- Z: the inverse dynamics function for the slave manipulator
- qs: the displacement of each joint of the slave manipulator
- $dqs/dt$, $d^2qs/dt^2$: the speed and acceleration are determined from a target value of the trajectory of the master manipulator.

10. The manipulation system having a force feedback capability according to claim 1, characterized in that the slave manipulator is controlled as follows:
   the target value of the drive torque of the pneumatically-driven system is calculated by using an equation comprising an inverse dynamics function of [Z(qs, dqs/dt, $d^2qs/dt^2$)]:
   wherein,
   - qs: the displacement of each joint of the slave manipulator
   - $dqs/dt$, $d^2qs/dt^2$: the speed and acceleration are determined from a target value of the trajectory of the master manipulator.

11. The manipulation system having a force feedback capability according to claim 1, characterized in that the slave manipulator is controlled as follows:
   the target value of the drive torque of the pneumatically-driven system is calculated by using an equation comprising dqs/dt and $d^2qs/dt^2$:
   wherein,
   - qs: the displacement of each joint of the slave manipulator
   - $dqs/dt$, $d^2qs/dt^2$: the speed and acceleration are determined from a target value of the trajectory of the master manipulator.

* * * * *